United States Patent [19]
Huang et al.

[11] Patent Number: 6,133,026
[45] Date of Patent: *Oct. 17, 2000

[54] CONDENSED PLASMID-LIPOSOME COMPLEX FOR TRANSFECTION

[75] Inventors: Shi Kun Huang, Castro Valley; Edwin Kiyoshi Oto, Redwood City; Mohammad Hassanipour, Vallejo; Bei Jin, Union City, all of Calif.

[73] Assignee: Sequus Pharmaceuticals, Inc., Menlo Park, Calif.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/151,436

[22] Filed: Sep. 11, 1998

Related U.S. Application Data

[63] Continuation-in-part of application No. 08/827,236, Mar. 28, 1997, Pat. No. 5,851,818, which is a continuation-in-part of application No. 08/657,795, May 31, 1996, abandoned.

[51] Int. Cl.$^7$ .......................... C12N 15/63; A01N 25/26; C07H 21/04; C12P 21/02
[52] U.S. Cl. ...................... 435/320.1; 424/417; 424/420; 427/231.3; 435/69.1; 536/23.1
[58] Field of Search ............................... 435/69.1, 320.1; 424/417, 420; 427/231.3; 514/44; 536/23.1

[56] References Cited

U.S. PATENT DOCUMENTS 5,851,818 12/1998 Huang et al. .................. 435/320.1

OTHER PUBLICATIONS

Hofland, H.E.J., et al., "Formation of Stable Cationic Lipid/DNA Complexes for Gene Transfer," *Proc. Natl. Acad. Sci. USA* 93:7305–7309 (1996).
Gao, X., and Huang, L., "Potentiation of Cationic Liposome–Mediated Gene Delivery by Polycations," *Biochem.* 35:1027–1036 (1996).
Li., S., and Huang, L., "Lipidic Supramolecular Assemblies for Gene Transfer," *J. Liposome Res.* 6(3):589–608 (1996).
Liu, Y., et al., "Cationic Liposome–Mediated Intravenous Gene Delivery," *J. Biol. Chem.* 270(42) :24864–24870 (1995).
Solodin, I., et al., "A Novel Series of Amphiphilic Imidazolinium Compounds for In Vitro and In Vivo Gene Delivery," *Biochem.* 34:13537–13544 (1995).
Thierry, A.R., et al., "Systemic Gene Therapy: Biodistribution and Long–Term Expression of a Transgene in Mice," *Proc. Natl. Acad. Sci. USA* 92:9742–9746 (1995).
Wagner, E., et al., "Transferrin–Polycation–DNA Complexes: The Effect of Pollycations on the Structure of the Complex and DNA Delivery to Cells," *Proc. Natl. Acad. Sci. USA* 88:4255–4259 (1991).
Xu, Y., and Szoka, F., *Biochemistry* 35:5616 (1996).
Xu et al. Biochemistry. 35: 5616–5623, 1996.
Orkin et al. Report & Recommendations of the Panel to Access the NIH Investment in Research on Gene Therapy, 1995.
Wasan. J Pham Sci 85(4):427–433, 1996.
Guo Liposome Research 3(1):51–70, 1993.
Hofland et al. Proc. Natl. Acad. Sci. 93: 7305–7309, 1996.
Gao et al. Biochemistry. 35: 1027–1036, 1996.
Li et al. J. Lipsome Research. 63 (3): 589–608, 1996.
Liu et al. Biol. Chem. 270 (42): 24864–24870, 1995
Solodin et al. Biochemistry. 34: 13537–13544, 1995.
Thierry et al. Proc. Natl. Acad. Sci. 92: 9742–9746, 1995.
Wagner et al. Proc. Natl. Acad. Sci. 88: 4255–4259, 1991.
Hong, K., et al., "Stabilization of cationic liposome–plasmid DNA complexes by polyamines and poly (ethylene glycol) –phospholipid conjugates for efficient in vivo gene delivery" FEBS Letters 400:233–237 (1997).

*Primary Examiner*—Robert A. Schwartzman
*Assistant Examiner*—Jon Shuman
*Attorney, Agent, or Firm*—Judy M. Mohr; Dehlinger & Associates

[57] ABSTRACT

A plasmid-liposome composition for transfection of a cell is described. The composition includes plasmid molecules condensed with a polycationic condensing agent and cationic liposomes. Also disclosed is a method for preparing the plasmid-liposome complexes.

14 Claims, 13 Drawing Sheets

CONDENSED PLASMID-LIPOSOME COMPLEX FOR TRANSFECTION

The present invention is a continuation-in-part application of U.S. patent application for patent, Ser. No. 08/827,236, filed Mar. 28, 1997 now U.S. Pat. No. 5,851,818, which is a continuation-in-part application of U.S. patent application for patent, Ser. No. 08/657,795, filed May 31, 1996, now abandoned.

FIELD OF THE INVENTION

The present invention relates to an improvement in a method for preparing plasmid-liposome complexes for in vivo transfection of a gene and to compositions prepared by the method.

REFERENCES

Felgner, J., et al., *Proc. Natl. Acad. Sci. USA* 84:7413–7417 (1987).
Felgner, J., et al., *J Tiss. Cult. Meth.* 15:63–68(1993).
Gao, X., and Huang, L., *Biochemistry* 35:1027–1036 (1996).
Guo, L., et al., *Journal of Liposome Research* 3(1):51–70 (1993).
Li, S., and Huang, L., *Journal of Liposome Research,* 6(3):589–608 (1996).
Mulligan, R. S., *Science* 260:926–932 (1993).
Morishita, R., et al., *J. Clin. Invest.* 91:2580–2585 (1993).
Rose, J. K., U.S. Pat. No. 5,279,833 (1994).
Trubetskoy, V. S., et al., *Biochimica et Biophysica Acta* 1131:311–313 (1992).
Wagner, E., et al., *Proc. Natl. Acad. Sci. USA* 88:4255–4259 (1991).

BACKGROUND OF THE INVENTION

A variety of methods have been developed to facilitate the transfer of genetic material into specific cells, e.g., gene therapy. These methods are useful for both in vivo or ex vivo gene transfer. In the former, a gene is directly introduced (intravenously, intraperitoneally, aerosol, etc.) into a subject. In ex vivo (or in vitro) gene transfer, the gene is introduced into cells after removal of the cells from specific tissue of an individual. The transfected cells are then introduced back into the subject.

Delivery systems for achieving in vivo and ex vivo gene therapy include viral vectors, such as a retroviral vector or adenovirus vectors, microinjection, electroporation, protoplast fusion, calcium phosphate, and liposomes (Felgner, et al., 1987; Mulligan, 1993; Morishita, et al., 1993).

Liposomal mediated gene therapy has, for example, involved the use of cationic liposomes formed from LIPOFECTIN, a reagent consisting of a cationic lipid and a neutral lipid (Felgner, et al., 1989, 1993). Other liposomal-mediated methods of gene therapy have been described (Trubetskoy, et al., 1992; Morishita, et al., 1993; Rose, 1994), where electrostatic complexes of cationic liposomes and DNA are formed. More recent approaches to liposome-based transfection compositions have included a polycation, such as protamine or polylysine, to bind the DNA to the lipid particles (Wagner, et al., 1991) or to condense the DNA (Gao and Huang, 1996; Li and Huang, 1996).

However, the liposomal-mediated gene therapy methods and compositions described to date have recognized limitations, including, for example, the toxicity of LIPOFECTIN, the large size of the DNA-liposome complexes, and rather poor in vivo transfection efficiencies.

It would be desirable, therefore, to produce a DNA plasmid-liposome complex which is relatively non-toxic, is sized for intravenous administration, and has a high transfection efficiency.

SUMMARY OF THE INVENTION

In one aspect, the invention includes a composition of plasmid-liposome complexes for use in transfecting a host cell with a gene contained in a plasmid. The composition includes plasmid molecules that are condensed with a polycationic condensing agent and suspended in a low-ionic strength aqueous medium and cationic liposomes formed of a cationic vesicle-forming lipid. The complexes have a ratio of liposome lipid to plasmid of greater than 5 nmole liposome lipid/$\mu$g plasmid and less than 25 nmole liposome lipid/$\mu$g plasmid and have a substantially homogeneous size of less than about 200 nm.

In one embodiment, the condensed plasmid molecules are DNA plasmid molecules containing a gene selected from the group consisting of genes encoding for cystic fibrosis transmembrane conductance regulator, Factor VIII, interleukin-2 or p53.

In one embodiment, the condensing agent is a polycation selected from histones, poly-l-glutamine, protamine, melittin and polymyxin B. In a preferred embodiment, the condensing agent is a histone selected from total histone, histone 1 and histone 4.

In another embodiment, the ratio of liposome lipid to plasmid is between 8–18 mole liposome lipid/$\mu$g plasmid.

The low-ionic strength aqueous medium is prepared from a non-ionic osmotic solute, such as glucose, sucrose or dextran.

The cationic liposomes are composed of a cationic vesicle-forming lipid selected from dimethyldioctadecylammonium (DDAB), 1,2-diolelyloxy-3-(trimethylamino) propane (DOTAP), N-[1-(2,3,-ditetradecyloxy)propyl]-N,N-dimethyl-N-hydroxyethylammonium bromide (DMRIE), N-[1-(2,3,-dioleyloxy)propyl]-N,N-dimethyl-N-hydroxy ethylammonium bromide (DORIE), N-[1-(2,3-dioleyloxy) propyl]-N,N,N-trimethylammonium chloride (DOTMA), and 3$\beta$[N-(N',N'-dimethylaminoethane) carbamoly] cholesterol (DC-Chol).

In another embodiment, the cationic liposomes further include a neutral vesicle-forming lipid. In still another embodiment, the cationic liposomes further include cholesterol.

In yet another embodiment, the cationic liposomes have a surface coating of hydrophilic polymer chains by including a vesicle-forming lipid derivatized with such a hydrophilic polymer. In one embodiment, at least a portion of the hydrophilic polymer chains are joined to the vesicle-forming lipid by a releasable bond, e.g., a bond effective to release the hydrophilic polymer chains in response to an existing or an induced physiologic condition. The plasmid-liposome complexes can further include a ligand attached to distal ends of the hydrophilic polymer chains for ligand-specific binding to a receptor molecule on a target cell surface. For example, and in a preferred embodiment, the hydrophilic polymer is polyethyleneglycol.

In another aspect, the invention includes, an improvement in a method of preparing a plasmid-liposome complex by condensing plasmid molecules and mixing the condensed plasmids with a suspension of cationic liposomes to form a plasmid-lipid complex for use in transfecting a host cell. The improvement includes (i) selecting as a condensing agent for condensing the plasmid molecules, a polycation selected from histones, poly-1-glutamine, protamine, melittin and polymyxin B, (ii) selecting as a medium for suspending the condensed plasmid molecules, a low-ionic strength aqueous medium, and (iii) selecting a ratio of liposome lipid to plasmid of greater than 5 nmole liposome lipid/μg plasmid and less than 25 nmole liposome lipid/μg plasmid. The plasmid-liposome complexes produced by the improvement have a substantially homogeneous size of less than 200 nm.

The plasmid-liposome complexes prepared according to the method of the invention, in one embodiment, are for use in transfecting a host cell with a gene contained in a DNA plasmid, where the DNA plasmid contains a gene selected from the group consisting of genes encoding for Factor VIII, interleukin-2 or p53.

In a preferred embodiment, the plasmid-liposome complex is for use in transfecting a host cell in the lung of a subject with a DNA plasmid containing cystic fibrosis transmembrane conductance regulator or, for lung carcinomas, cytokines, such as interleukin-2, or tumor suppressor genes, such as p53.

These and other objects and features of the invention will become more fully apparent when the following detailed description of the invention is read in conjunction with the accompanying drawings.

DETAILED DESCRIPTION OF THE INVENTION

I. Plasmid-Liposome Complex

Figure 1:
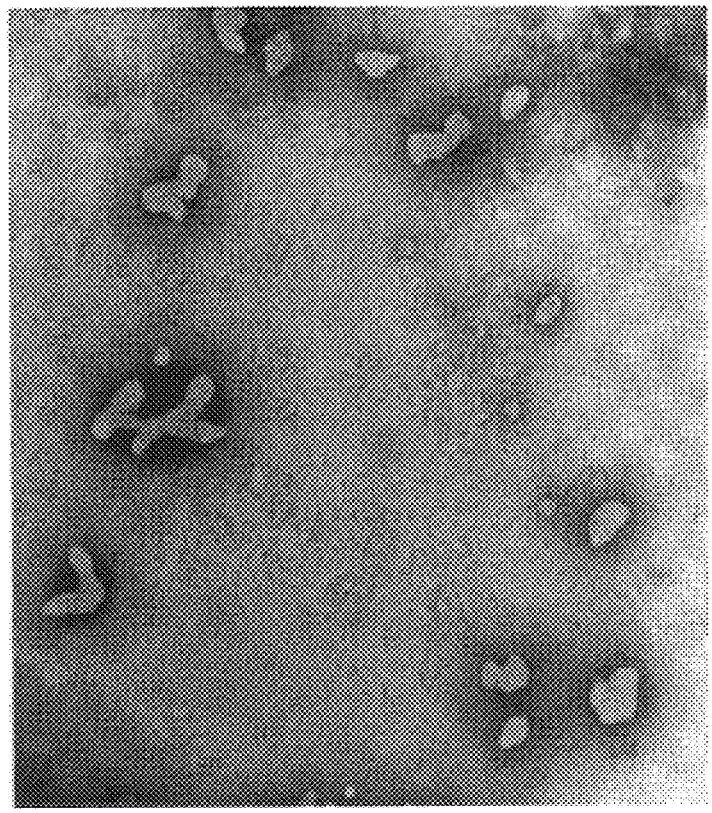
FIG. 1 is a computer-generated image of an electron micrograph of a plasmid condensed with the polycationic polymer total histone.

The present invention is directed to a plasmid-liposome complex, and to an improvement in a method of preparing such a complex, for use in in vivo transfection of a host cell. The composition includes plasmid molecules which are condensed with a polycationic condensing agent and then suspended in low-ionic strength medium. The condensed plasmid molecules are mixed with lipid particles, such as liposomes, to form plasmid-liposome complexes. The improvement in the method of preparation, as will be described, relates to selection of the condensing agent, selection of the suspension medium and selection of the liposome lipid to plasmid ratio. Before describing the improved preparation procedure in detail, the plasmid-liposome complex and its components will be described.

A. Cationic Liposome Components and Preparation

As described above, the plasmid-liposome complex includes condensed plasmid molecules and liposomes. Liposomes, as used herein, refer to lipid vesicles having an outer lipid shell, typically formed on one or more lipid bilayers, encapsulating an aqueous interior. In a preferred embodiment, the liposomes are cationic liposomes composed of between about 20–80 mole percent of a cationic vesicle-forming lipid, with the remainder neutral vesicle-forming lipids and/or other components. As used herein, "vesicle-forming lipid" refers to any amphipathic lipid having hydrophobic and polar head group moieties and which by itself can form spontaneously into bilayer vesicles in water, as exemplified by phospholipids. A preferred vesicle-forming lipid is a diacyl-chain lipid, such as a phospholipid, whose acyl chains are typically between about 14–22 carbon atoms in length, and have varying degrees of unsaturation.

A cationic vesicle-forming lipid is one whose polar head group with a net positive charge, at the operational pH, e.g., pH 4–9. Typical examples include phospholipids, such as phosphatidylethanolamine, whose polar head groups are derivatized with a positive moiety, e.g., lysine, as illustrated, for example, for the lipid DOPE derivatized with L-lysine (LYS-DOPE) (Guo, et al., 1993). Also included in this class are the glycolipids, such as cerebrosides and gangliosides having a cationic polar head-group.

Another cationic vesicle-forming lipid which may be employed is cholesterol amine and related cationic sterols. Exemplary cationic lipids include 1,2-diolelyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3β[N-(N',N'-dimethylaminoethane) carbamoyl] cholesterol (DC-Chol); and dimethyldioctadecylammonium (DDAB).

The remainder of the liposomes are formed of neutral vesicle-forming lipids, meaning vesicle forming lipids which have no net charge or which may include a small percentage of lipids having a negative charge in the polar head group. Included in this class of lipids are the phospholipids, such as phosphatidylcholine (PC), phosphatidyl ethanolamine (PE), phosphatidylinositol (PI), and sphingomyelin (SM), and cholesterol, cholesterol derivatives, and other uncharged sterols.

The above-described lipids can be obtained commercially, or prepared according to published methods. Other lipids that can be included in the invention are glycolipids, such as cerebrosides and gangliosides.

In one embodiment of the invention, the plasmid-liposome complex includes liposomes having a surface coating of hydrophilic polymer chains, effective to extend the blood circulation time of the plasmid/liposome complexes. Suitable hydrophilic polymers include polyethylene glycol (PEG), polylactic acid, polyglycolic acid, polyvinyl-pyrrolid-one, polymethyloxazoline, polyethyloxazoline, polyhydroxypropyl methacrylamide, polymethacrylamide, polydimethylacrylamide, and derivatized celluloses, such as hydroxymethylcellulose or hydroxyethyl-cellulose. A preferred hydrophilic polymer chain is polyethyleneglycol (PEG), preferably as a PEG chain having a molecular weight between 500–10,000 daltons, more preferably between 1,000–5,000 daltons. The hydrophilic polymer may have solubility in water and in a non-aqueous solvent, such as chloroform.

The coating is preferably prepared by including in the vesicle-forming lipids forming the liposomes, between 1–20 mole percent of a vesicle-forming lipid, preferably a phospholipid or other diacyl-chain lipid, derivatized at its head group with the polymer chain. Exemplary methods of preparing such lipids, and forming polymer coated liposomes therewith, have been described in co-owned U.S. Pat. Nos. 5,013,556, and 30 5,395,619, which are incorporated herein by reference.

It will be appreciated that the hydrophilic polymer can be stably coupled to the lipid, or coupled through an unstable linkage which allows the polymer-coated plasmid-liposome complexes to shed or "release" the hydrophilic polymer coating during circulation in the bloodstream or after localization at a target site. Attachment of hydrophilic polymers, in particular polyethyleneglycol (PEG), to vesicle-forming lipids through a bond effective to release the polymer chains in response to a stimulus have been described, for example in WO 98/16202, WO 98/16201, which are hereby incorporated by reference, and by Kirpotin, D. et a. (*FEBS Letters*, 388:115–118 (1996).

The releasable linkage, in one embodiment, is a chemically releasable linkage which is cleaved by administration of a suitable releasing agent or is cleaved under selective physiological conditions, such as in the presence of enzymes or reducing agents. For example, ester and peptide linkages are cleaved by esterase or peptidase enzymes. Disulfide linkages are cleaved by administration of a reducing agent, such as glutathione or ascorbate, or by a reducing agent present in vivo, such as cysteine, which is present in plasma and intracellularly.

Other releasable linkages include pH sensitive bonds and bonds which are cleaved upon exposure to glucose, light or heat. By way of an example, the hydrophilic polymer chains can be attached to the liposome by a pH sensitive bond, and the plasmid-liposome complexes are targeted to a site having a pH effective to cleave the bond and release the hydrophilic chains, such as a tumor region. Exemplary pH sensitive bonds include acyloxyalkyl ether, acetal and ketal bonds. Another example is where the cleavable bond is a disulfide bond, broadly intended herein to refer to sulfur-containing bonds. Sulfur-containing bonds can be synthesized to achieve a selected degree of lability and include disulfide bonds, mixed sulfide-sulfone bonds and sulfide-sulfoxide bonds. Of the three bonds, the disulfide bond is least susceptible to thiolysis and the sulfide-sulfoxide bond is most susceptible.

Such releasable bonds are useful to tailor the rate of release of the hydrophilic polymer segment from the plasmid-liposome complexes. For example, a very labile disulfide bond can be used for targeting to blood cells or endothelial cells, since these cells are readily accessible and a shorter liposome blood circulation lifetime is sufficient. At the other extreme, a long-lasting or hearty disulfide bond can be used when the target is tumor tissue or other organs where a longer liposome blood circulation lifetime is generally needed for the complexes to reach the desired target.

The releasable bond attaching the hydrophilic polymer chains to the liposome is cleaved in vivo typically as a result of change in environment, such as when the liposomes reach a specific site with a slightly lower pH, such as a region of tumor tissue, or a site with reducing conditions, such as a hypoxic tumor. Reducing conditions in vivo can also be effected by administration of a reducing agent, such as ascorbate, cysteine or glutathione. The cleavable bond may also be broken in response to an external stimuli, such as light or heat.

In another embodiment, the plasmid-liposome complexes include an affinity moiety or targeting ligand effective to bind specifically to target cells at which the therapy is aimed. Such moieties can be attached to the surface of the liposome or to the distal ends of hydrophilic polymer chains. Exemplary moieties include antibodies, ligands for specific binding to target cell surface receptors and the like, as described, for example, in PCT application Nos. WO US94/03103, WO 98/16202 and WO 98/16201. The moiety can also be a hydrophobic segment to facilitate fusion of the complex with a target cell.

B. Condensed Plasmid

This section describes the preparation of the condensed-phase plasmid employed in the plasmid-liposome complex of the invention.

Polycationic condensing agents used to condense the plasmid are multiply charged cationic polymers, typically biopolymers such as such as spermidine, spermine, polylysine, protamine, total histone, specific histone fractions such as H1, H2, H3, H4, and other polycationic polypeptides, but may also include biocompatible polymers, such as polymyxin B. It will be appreciated that these polycationic condensing agents can be used in free base or salt forms, for example, protamine sulfate and polylysine hydrobromide. In a preferred embodiment, the polycationic condensing agent is a histone, which, as referred to herein, includes total histone or specific histone fractions.

Plasmids suitable for use in the complex are preferably circularized or closed double-stranded molecules having sizes preferably in the 5–40 Kbp (kilo basepair) range. The plasmids are constructed according to well-known methods and include a therapeutic gene, i.e., the gene to be expressed in gene therapy, under the control of suitable promoter and terminator control elements, and other elements necessary for replication within the host cell and/or integration into the host-cell genome. Methods for preparing plasmids useful for gene therapy in genes or other mammals are widely known and referenced.

The genes to be introduced for gene therapy by the complex of the invention generally fall into one of three categories:

In the first are those genes which are intended to overcome a gene deficiency or defect in the subject, i.e., where the subject fails to produce active, endogenous protein at all or within normal levels, and the gene introduced in the plasmid is intended to make up this deficiency. Examples of this class of genes include genes encoding adenosine deaminase (ADA), for gene expression in stem cells or lymphocytes; genes encoding purine nucleoside phosphorylase deficiency, deficiency in prostaglandin G/H synthase, therapy of Lesch-Nyhan syndrome caused by a deficiency in hypoxanthine-guanine phosphoribosyltransferase, genes encoding a variety of circulating proteins, such as $\alpha_1$-antitrypsin, clotting factors (e.g., Factor VIII, Factor IX) and globins (e.g., β-globin, hemoglobin), for the treatment of hemophilia, sickle-cell anemia and other blood-related diseases, and genes encoding hormones and other peptide regulators.

In the second class are polypeptides designed to treat any existing pathology, such as cancer, or a pathogenic condition such as viral infection. Examples include gene therapy to supply the p53 gene for cancer therapy, the gene for the CD4 peptide to inhibit HIV infection, the gene for the Pseudomonas peptide to inhibit binding of Pseudomonas to epithelial cells, and specific antibody genes to inhibit a targeted pathogen.

The third class includes genes intended to produce an mRNA transcript that can act as an antisense molecule to inhibit an undesirable protein expression, such as overexpression of proteins specific for tumor growth, or expression of viral proteins.

II. Preparation and Characterization of the Complex

In accordance with the invention, it has been discovered that a plasmid-liposome complex formed by mixing condensed-phase plasmid and cationic liposomes, in a low ionic strength medium, produces complexes having a substantially homogeneous size of typically less than about 200 nm and preferably in the range of 50–200 nm, more preferably between 100–200 and most preferably between 120–180 nm. The complexes are further characterized by a retention of activity of the expression of the encoded gene, that is, the complexes have a transfection stability. This is evidenced by the ability of the complexes after storage for 30 days, and preferably 90 days, at 4° C., to transfect cells and achieve expression of the encoded gene, as will be discussed below.

The condensed-phase plasmid is formed by adding to the plasmid, in a low-ionic strength medium, a polycationic polymer condensing agent of the type identified above. The cationic polymer is added to the plasmid solution to a preferred concentration at which charge stoichiometry is achieved, i.e., where the total number of charges in the cationic polymer (as determined from the polymer's known charge density/weight) is at least as great as the total negative charge of the DNA (as determined from the weight amount plasmid and the known charge density of DNA/weight). Typically, the weight ratio of added DNA plasmid to added polymer is between about 0.1–5.0, more preferably, between 0.3–2.0. The condensing agent is preferably added slowly to the plasmid suspension with stirring, e.g., over a 10 minute period.

The condensed plasmid and cationic liposomes, both contained in a low-ionic strength medium, are then mixed, e.g., by slow addition of the condensed plasmid molecules to the liposomes. The ratio of liposome lipids to plasmid is an important parameter for achieving maximum transfection. That ratio, in nmole liposome lipid/μg plasmid, is greater than 5 but less than 25, preferably greater than 8 but less than 18, more preferably greater than 10 but less than 15 and most preferably between 12–14.

As indicated above, a critical feature of the invention is the mixing of liposomes and condensed phase plasmid in a low ionic-strength medium. Preferably the final concentration of the medium, including ions present in the DNA, condensing agent, and liposome lipid species, is less than the ionic strength of a 25 mM monovalent ionizable salt, such as NaCl, and preferably less than 10 mM of such salt, more preferably less than about 1 mM. In general, low ionic strength is readily obtained by employing free base or free acid plasmid, polycation, and lipid species, removing electrolyte components, or alternatively, employing sufficiently dilute concentrations of the components to maintain a low ionic strength, and/or removing electrolytes generated from the components by dialysis or the like. At the same time, it is useful to prepare the composition in the presence of a non-electrolyte solute such as glucose to provide an osmotic balance as an injectable formulation.

FIG. 1 is a computer-generated image of a negative-stain transmission electron micrograph of a luciferase-encoding pNSL plasmid condensed with total histone, prepared as described in Example 1. As seen, the plasmid is condensed into discrete, single particles of about 100 nm in diameter and less.

Figure 2:
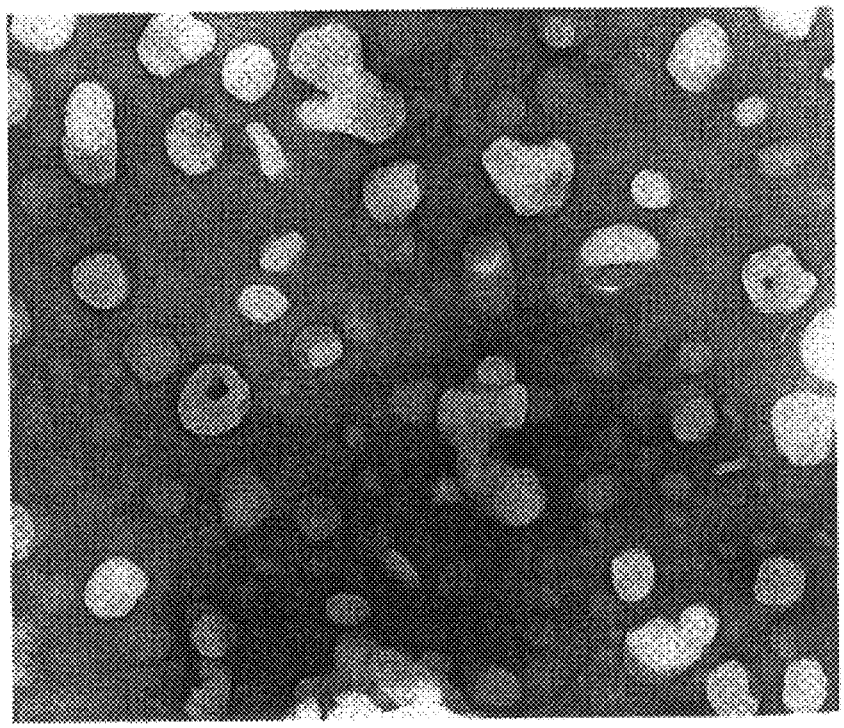
FIG. 2 is a computer-generated image of an electron micrograph of a polycation-condensed plasmid complexed with cationic liposomes in accordance with the invention.

FIG. 2 is a computer-generated image of a negative-stain transmission electron micrograph of a polycation-condensed plasmid-liposome complex prepared as described in Example 1. In comparing the neat, condensed plasmid molecules in FIG. 1 with the complex of FIG. 2, the opaque, condensed plasmids are readily apparent in FIG. 2. Also visible in FIG. 2 is a transparent membrane which surrounds each condensed plasmid. This transparent membrane is the liposome lipid bilayer which coats each condensed plasmid.

Figure 3A:
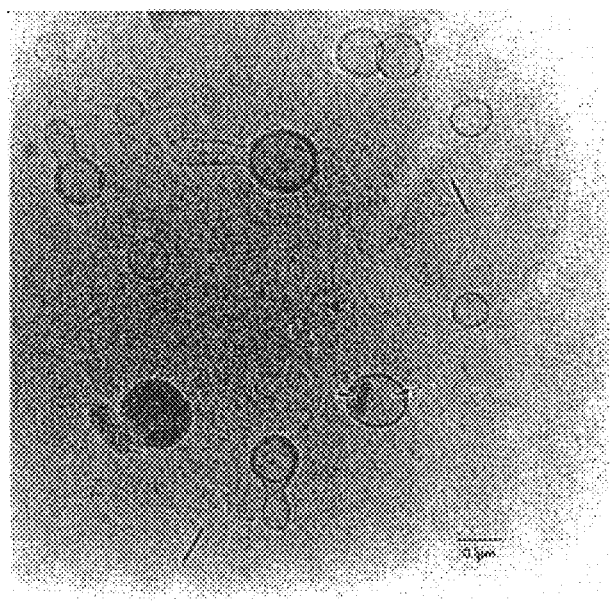
FIGS. 3A–3B are computer-generated images of cryogenic (FIG. 3A) and freeze fracture (FIG. 3B) transmission electron micrographs of a polycation-condensed plasmid complexed with cationic liposomes in accordance with the invention.
Figure 3B:
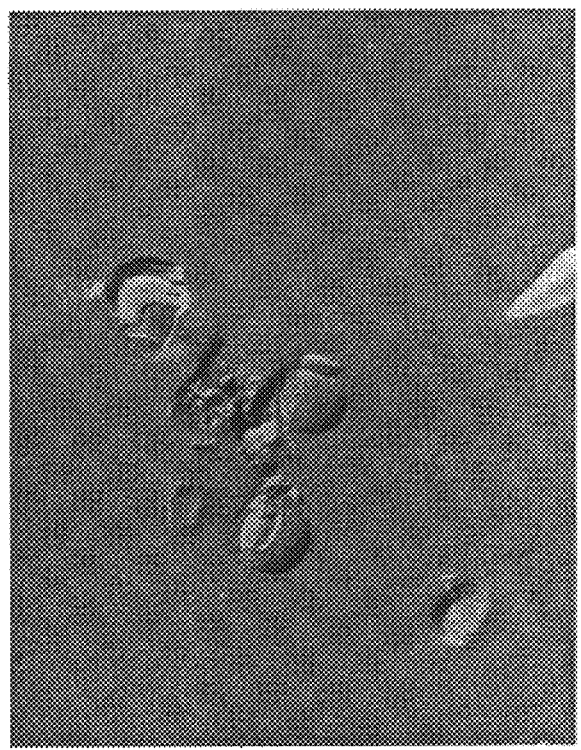

FIGS. 3A–3B are computer-generated images of cryo-electron and freeze fracture transmission electron micrographs of the plasmid-liposome complex prepared as described in Example 1. The micrograph in FIG. 3A is obtained by freezing a thin layer of plasmid-liposome complex suspension and viewing the layer under a cryoelectro microscope. The micrograph shows single, discrete plasmid-liposome complexes, where the condensed DNA is visible as a darker central region in many of the particles. The freeze-fracture micrograph of FIG. 3B also shows discrete plasmid-liposome complexes, with no apparent aggregation.

Figure 4:
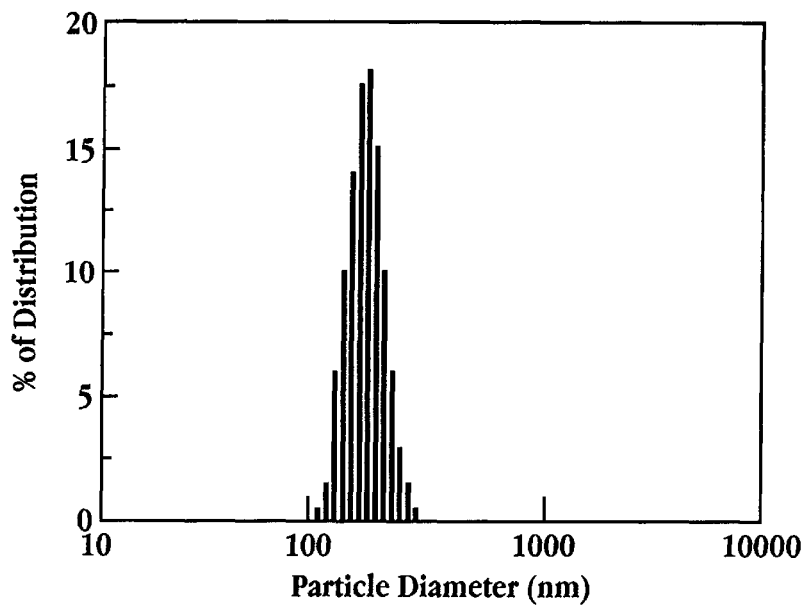
FIG. 4 is a plot showing the size, in nm as measured by dynamic light scattering, of plasmid-liposome complexes prepared in accordance with the invention.

Dynamic light scattering was used to determine the average complex size and size distribution. The results are shown in FIG. 4 which shows that the complexes as prepared in Example 1 form a homogeneous population having an average size of about 146 nm (standard deviation of 45 rim). This and other studies performed in support of the invention indicate that the composition when prepared according to the described method achieves complexes have a homogeneous population, as evidenced by a single peak indicating a population of complexes having a relatively narrow size distribution. Preferably, complexes have a size of less than 200 nm, more preferably between 50–200 rim, most preferably between 100–200 and still more preferably between 120–180 nm.

Figure 5:
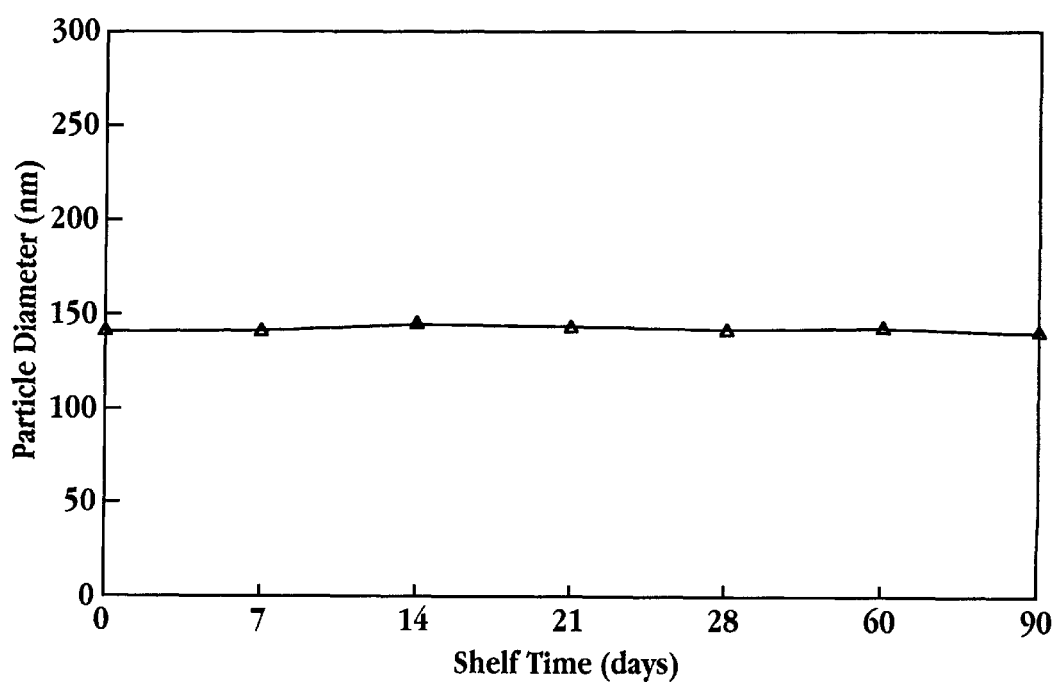
FIG. 5 is a plot of particle diameter, in nm as measured by dynamic light scattering, as a function of storage time at 4 C, for plasmid-liposome complexes of the invention.

As briefly discussed above, the plasmid-liposome complexes are stable, that is, the complexes maintain their initial size, e.g., there is little aggregation of the complexes, and the complexes retain therapeutic activity, for at least 30 days after storage at 4° C. FIG. 5 provides evidence of complex size stability and shows the complex size, as measured by dynamic light scattering, as a function of time. A suspension of the plasmid-liposome complexes in water/glucose were stored at 4° C. and analyzed after 7, 14, 21, 28, 60 and 90 days of storage. Initially after complex formation, the average complex size was about 150 rim and, as seen, after 90 days of storage, the complex size remained at about 150 nm. Complex stability with respect to retention of therapeutic activity is discussed below in FIGS. 11A–11B.

III. In vivo Transfection

Plasmid-liposome complexes prepared in accordance with the invention were administered to mice to determine the transfection efficiency of various plasmid-liposome complex formulations and to determine stability of transfection, biodistribution of the complex, pharmacokinetics and dose response. The exemplary in vivo transfection procedure is described in Example 2.

Figure 6:
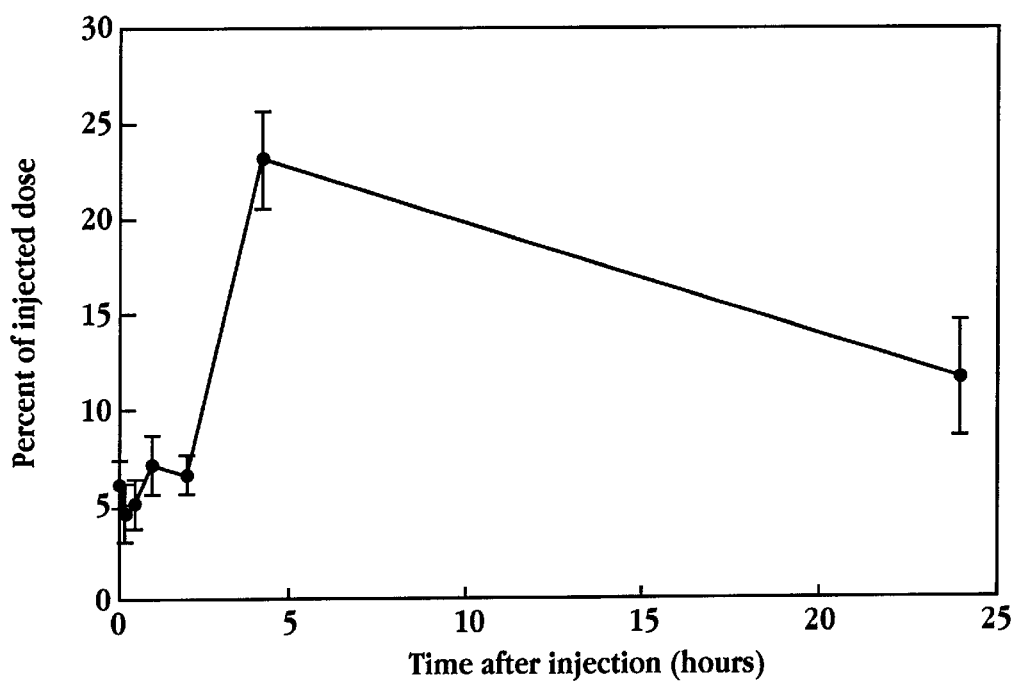
FIG. 6 is a plot of percent of injected dose as a function of time after intravenous injection in mice of labeled plasmid-liposome complexes of the invention.

The pharmacokinetics of plasmid-liposome complexes were determined by injecting complexes including an $S^{35}$-labelled DNA plasmid into mice. FIG. 6 shows the percent of injected dose as a function of time after intravenous injection. Immediately after injection of the plasmid-liposome complex, about 7% of the injected dose is in the blood stream. Other studies have determined that the remaining percentage of the complexes localize in the lung immediately after injection. After a period of time the complexes are neutralized by serum proteins in the lung and enter the blood stream, as evidenced by the increase in the percentage of injected dose to about 22% at the 5 hour time point (FIG. 6). The complexes are then cleared from the bloodstream, with about 12% of the injected dose present at 24 hours.

Plasmid-liposome complexes were prepared for in vivo administration with varying ratios of liposome lipid to plasmid. The complexes were prepared according to the general procedure set forth in Example 1 by varying the amount of polycation condensing agent, and the total amount of liposome lipids. Typically, the amount of polycation condensing agent varied between 100–500 µg and the liposome lipid/plasmid ratio varied between 8–18 nmoles lipid/µg plasmid.

FIGS. 7–9 show the results for plasmid-liposome complexes prepared with total histone (FIGS. 7A–7E), histone H1 (FIGS. 8A–8E) and histone H4 (FIGS. 9A–9E) as the polycationic condensing agents. After administration of the complex, prepared from the formulations indicated in the tables below, luciferase expression was measured in the lung, liver, heart, spleen and kidney.

Table 1 summarizes the compositions for the plasmid-liposome complexes prepared using total histone as the polycationic condensing agent. The amount of total histone was varied between 100–500 µg to vary the ratio of plasmid/total histone from 0.2–1.0. The ratio of liposome lipids/plasmid was also varied and ratios of 8, 14 and 18 nmoles liposome lipids/µg plasmid were tested.

TABLE 1

| Component | Formulation Number[1] | | | | | |
|---|---|---|---|---|---|---|
| | 1 | 2 | 3 | 4 | 5 | 6 |
| pNSL plasmid, µg | 100 | 100 | 100 | 100 | 100 | 100 |
| total histone, µg | 200 | 100 | 200 | 350 | 500 | 200 |
| µmoles liposomes lipids[2] | 0.8 | 1.4 | 1.4 | 1.4 | 1.4 | 1.8 |
| µg plasmid/µg total histone | 0.5 | 1.0 | 0.5 | 0.3 | 0.2 | 0.5 |
| nmoles lipids/µg plasmid | 8 | 14 | 14 | 14 | 14 | 18 |

[1] In vivo results for each formulation number in FIGS. 7A–7E.
[2] Liposome prepared from 1:1 mole ratio of DDAB:cholesterol.

Figure 7A:
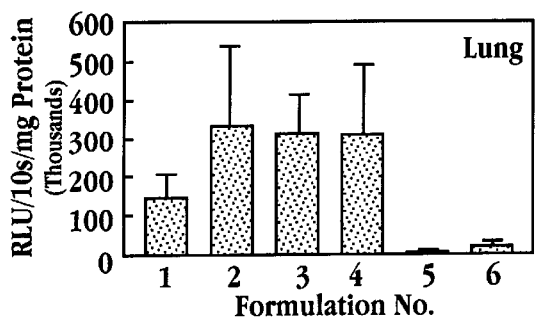
FIGS. 7A–7E show luciferase expression, in relative light units (RLU)/10 seconds/mg protein, in the lung (FIG. 7A), liver (FIG. 7B), heart (FIG. 7C). spleen (FIG. 7D) and kidney (FIG. 7E) for plasmid-liposome complexes prepared with total histone.
Figure 7B:
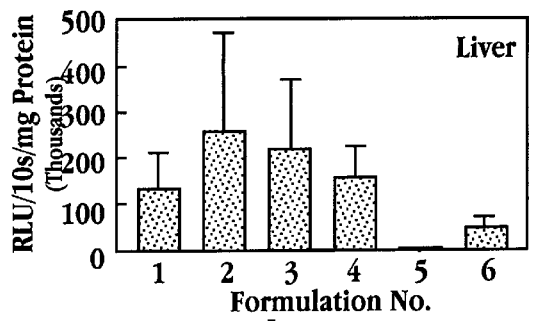
Figure 7C:
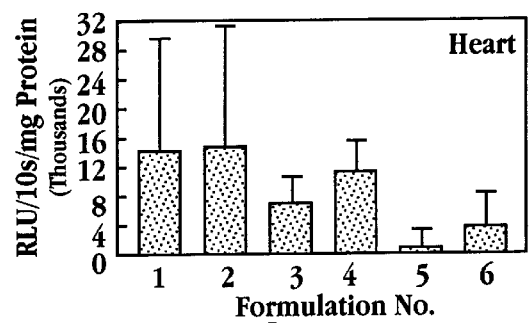
Figure 7D:
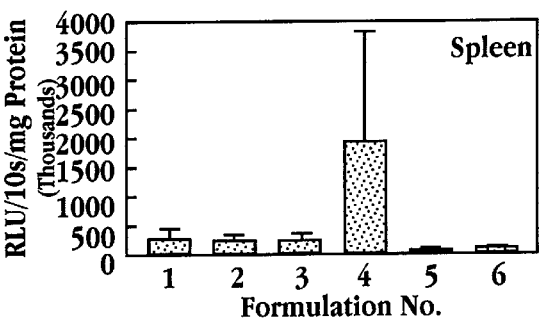
Figure 7E:
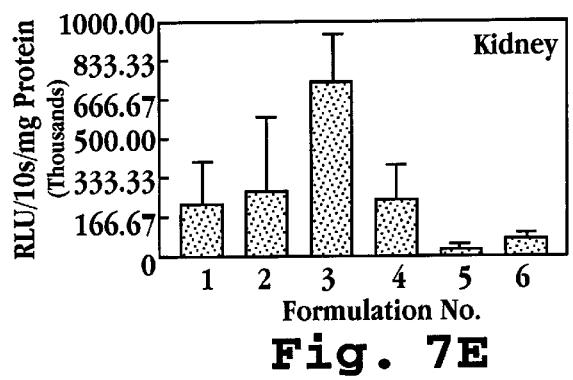

The results of in vivo administration in mice of the formulations summarized in Table 1 are shown in FIGS. 7A–7E, where luciferase expression, in relative light units (RLU)/10 seconds/mg protein, is shown in the lung (FIG. 7A), liver (FIG. 7B), heart (FIG. 7C), spleen (FIG. 7D) and kidney (FIG. 7E). The figures indicate that there is a window where the transfection is highest. Specifically, for total histone as the condensing agent, the transfection is highest where the liposome lipid/plasmid ratio is greater than 8 nmoles lipid/µg plasmid and less than 18 nmoles lipid/µg.

Table 2 summarizes the plasmid-liposome complex compositions prepared and tested in vivo using histone H1 as the polycationic condensing agent. The ratio of plasmid/histone H1 ratio was 0.3 or 0.5 and the liposome lipid/plasmid ratio was varied from 8, 14 and 18 nmoles lipid/µg plasmid.

TABLE 2

| Component | Formulation Number[1] | | | | |
|---|---|---|---|---|---|
| | 7 | 8 | 9 | 10 | 11 |
| pNSL plasmid, µg | 100 | 100 | 100 | 100 | 100 |
| histone H1, µg | 350 | 200 | 350 | 200 | 350 |
| µmoles liposome lipids[2] | 0.8 | 1.4 | 1.4 | 1.4 | 1.4 |
| µg plasmid/µg histone H1 | 0.3 | 0.5 | 0.3 | 0.5 | 0.3 |
| nmoles lipids/µg plasmid | 8 | 14 | 14 | 18 | 18 |

[1] In vivo results for each formulation number shown in FIGS. 8A–8E.
[2] Liposomes prepared from 1:1 mole ratio of DDAB:cholesterol.

Figure 8A:
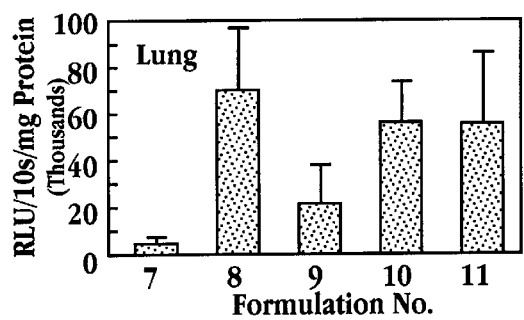
FIGS. 8A–8E show luciferase expression, in relative light units (RLU)/10 seconds/mg protein, in the lung (FIG. 8A), liver (FIG. 8B), heart (FIG. 8C), spleen (FIG. 8D) and kidney (FIG. 8E) for plasmid-liposome complexes prepared with histone H1.
Figure 8B:
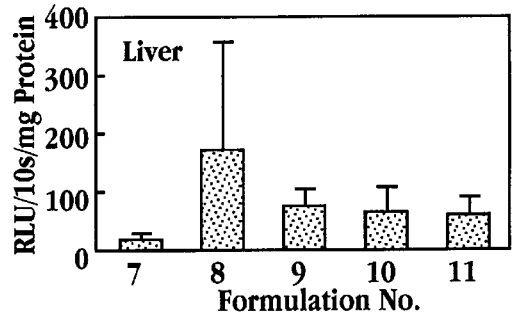
Figure 8C:
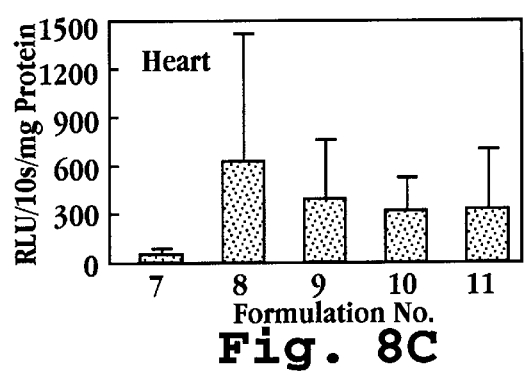
Figure 8D:
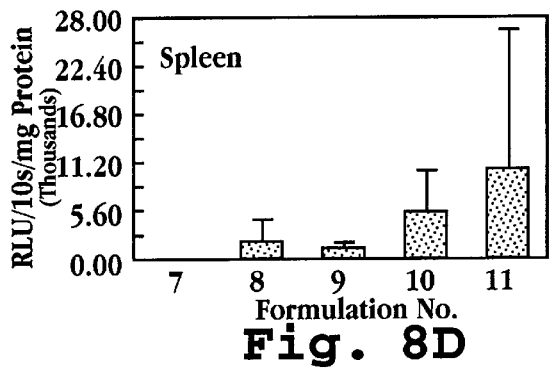
Figure 8E:
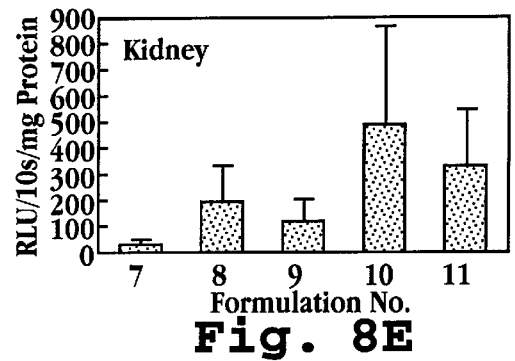

The results of in vivo administration in mice of the formulations summarized in Table 2 are shown in FIGS. 8A–8E, where luciferase expression, in relative light units (RLU)/10 seconds/mg protein, is shown in the lung (FIG. 8A), liver (FIG. 8B), heart (FIG. 8C), spleen (FIG. 8D) and kidney (FIG. 8E). The figures indicate that the best transfection is achieved at a liposome lipid/plasmid ratios of 14 and 18.

Tables 3A and 3B summarize the formulations of plasmid-liposome complexes formed using histone H4 as the polycationic condensing agent. The plasmid/histone H4 ratio varied from 0.2, 0.3 or 0.5 and the liposome lipid/plasmid ratio was varied from 8, 14 or 18 nmoles lipid/µg plasmid.

TABLE 3A

| Component | Formulation Number[1] | | | |
|---|---|---|---|---|
| | 12 | 13 | 14 | 15 |
| pNSL plasmid, µg | 100 | 100 | 100 | 100 |
| histone H4, µg | 200 | 350 | 500 | 200 |
| µmoles liposome lipids[2] | 0.8 | 0.8 | 0.8 | 1.4 |
| µg plasmid/µg histone H4 | 0.2 | 0.3 | 0.2 | 0.5 |
| nmoles lipids/µg plasmid | 8 | 8 | 8 | 14 |

[1]In vivo results for each formulation number shown in FIGS. 9A–9E.
[2]Liposomes prepared from 1:1 mole ratio of DDAB:cholesterol.

TABLE 3B

| Component | Formulation Number[1] | | | | |
|---|---|---|---|---|---|
| | 16 | 17 | 18 | 19 | 20 |
| pNSL plasmid, µg | 100 | 100 | 100 | 100 | 100 |
| histone H4, µg | 350 | 500 | 200 | 350 | 500 |
| µmoles liposome lipids[2] | 1.4 | 1.4 | 1.8 | 1.8 | 1.8 |
| µg plasmid/µg histone H4 | 0.3 | 0.2 | 0.5 | 0.3 | 0.2 |
| nmoles lipids/µg plasmid | 14 | 14 | 18 | 18 | 18 |

[1]In vivo results for each formulation number shown in FIGS. 9A–9E.
[2]Liposomes prepared from 1:1 mole ratio of DDAB:cholesterol.

Figure 9A:
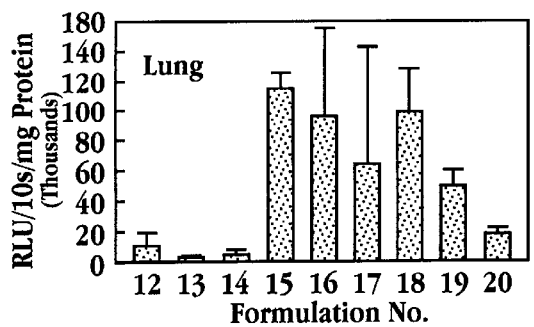
FIGS. 9A–9E show luciferase expression, in relative light units (RLU)/10 seconds/mg protein, in the lung (FIG. 9A), liver (FIG. 9B), heart (FIG. 9C), spleen (FIG. 9D) and kidney (FIG. 9E) for plasmid-liposome complexes prepared with histone H4.
Figure 9B:
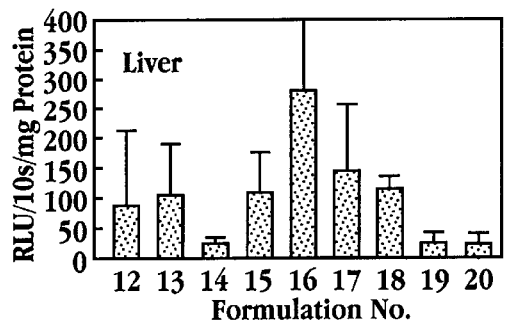
Figure 9C:
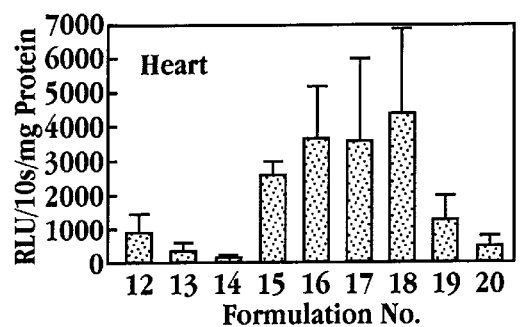
Figure 9D:
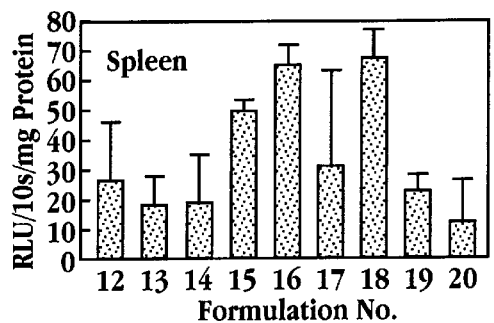
Figure 9E:
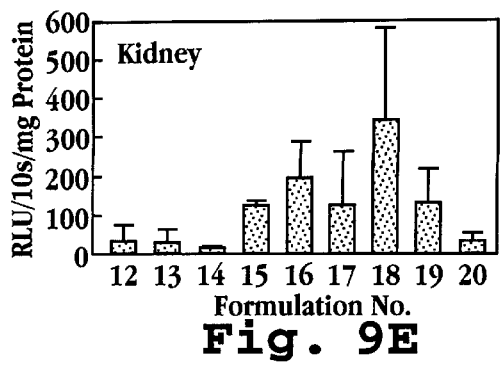

The results of in vivo administration in mice of the formulations summarized in Tables 3A and 3B are shown in FIGS. 9A–9E, where luciferase expression, in relative light units (RLU)/10 seconds/mg protein, is shown in the lung (FIG. 9A), liver (FIG. 9B), heart (FIG. 9C), spleen (FIG. 9D) and kidney (FIG. 9E). There is a window where transfection is highest of greater than 8 nmoles liposome lipid/µg plasmid and less than 18 nmoles liposome lipid/µg plasmid.

In other experiments performed in support of the present invention, plasmid-liposome complexes were prepared using poly-l-glutamine, melittin (a low molecular weight peptide containing 26 amino acids) or polymyxin B sulfate as polycationic condensing agents. Each of these are commercially available from Sigma Chemical Co. The complexes were injected in mice, as described Example 2, and in vivo transfection was measured by determining luciferase expression.

Table 4 summarizes the plasmid-liposome complex compositions prepared using poly-l-glutamine, melittin or polymyxin B as polycationic condensing agents. The amount of condensing agent was varied from 50–200 µg.

Figure 10A:
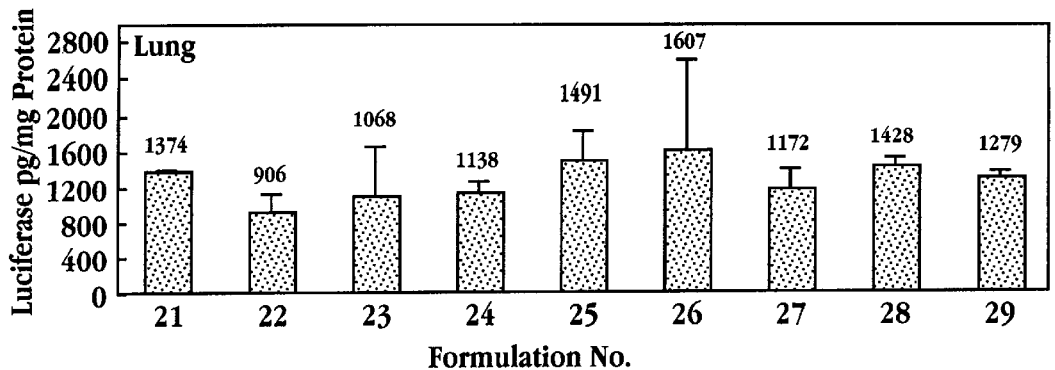
FIGS. 10A–10E show luciferase expression, in pg luciferase/mg protein, in the lung (FIG. 10A), liver (FIG. 10B), heart (FIG. 10C), spleen (FIG. 10D) and kidney (FIG. 10E) for plasmid-liposome complexes prepared with poly-l-glutamine, melittin or polymyxin B as the cationic condensing agent.
Figure 10B:
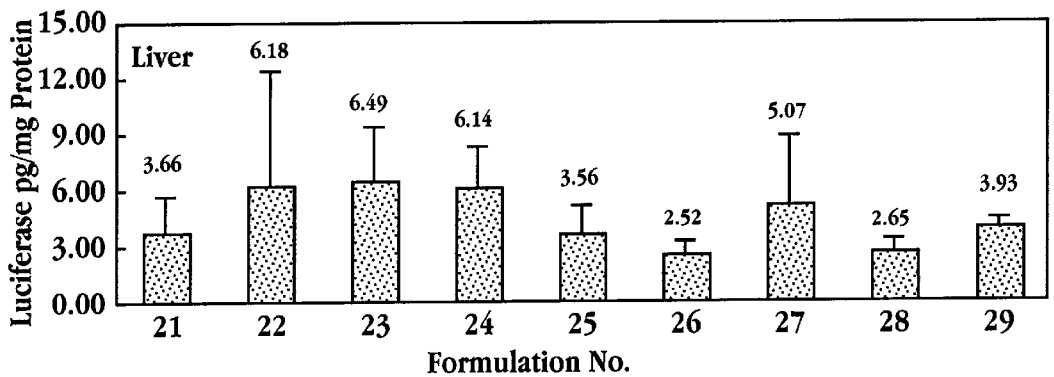
Figure 10C:
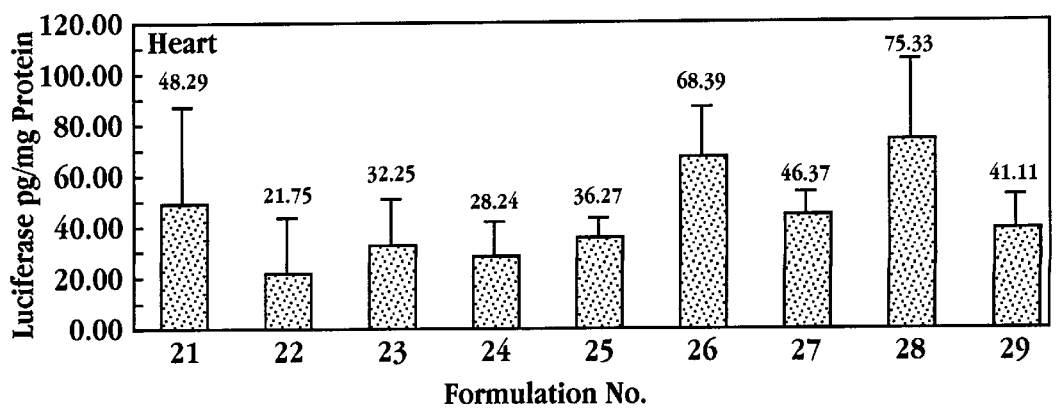
Figure 10D:
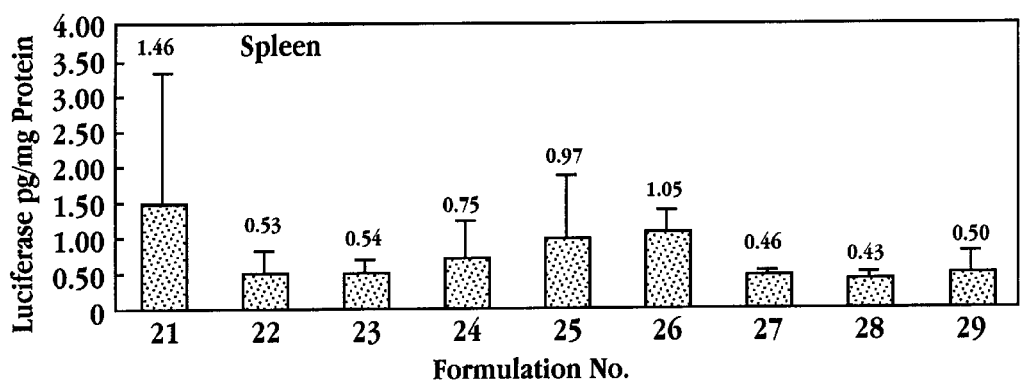
Figure 10E:
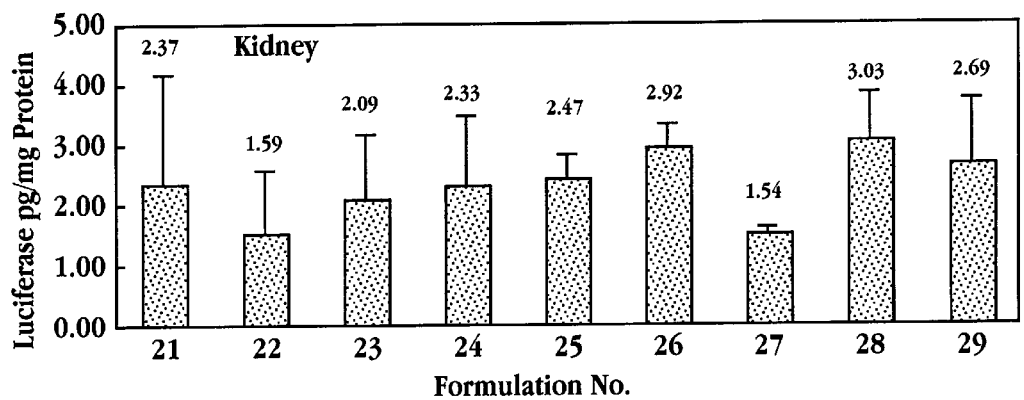

The results of in vivo administration in mice of the plasmid-liposome complexes in Table 4 are shown in FIGS. 10A–10E, where luciferase expression, in pg luciferase/mg protein, is shown in the lung (FIG. 10A), liver (FIG. 10B), heart (FIG. 10C), spleen (FIG. 10D) and kidney (FIG. 10E). The lipid/plasmid ratio for each of the formulations was constant at 14 nmoles lipid/µg plasmid, falling about midway in the preferred range of 5–25 nmoles liposome lipid/µg plasmid.

These studies using a variety of polycationic condensing agents, e.g., total histone, histone H1, histone H4, poly-l-glutamine, melittin and polymyxin B, indicate that transfection is achieved when the liposome lipid/plasmid ratio (in nmoles lipid/µg plasmid) is greater than 5 and less than about 25. More preferably, the ratio is between 8–18, even more preferably between 10–15 and most preferably between 12–14 nmoles liposome lipid/µg plasmid.

As discussed above, the plasmid-liposome complex of the present invention is stable, as evidenced by little change in particle size (see FIG. 5), for as long as 90 days at 4° C. The expression stability of the complex was determined by administering plasmid-liposome complexes which were stored at 4° C. to mice. Specifically, the suspension of plasmid-liposome complexes was administered intravenously to mice immediately after preparation of the complex (day 0) and at 7, 14, 21, 28, 30 and 90 days after storage at 4° C. Following the procedure detailed in Example 2, luciferase expression in the lung and liver was determined, and the results are shown in FIGS. 11A–11B.

Figure 11A:
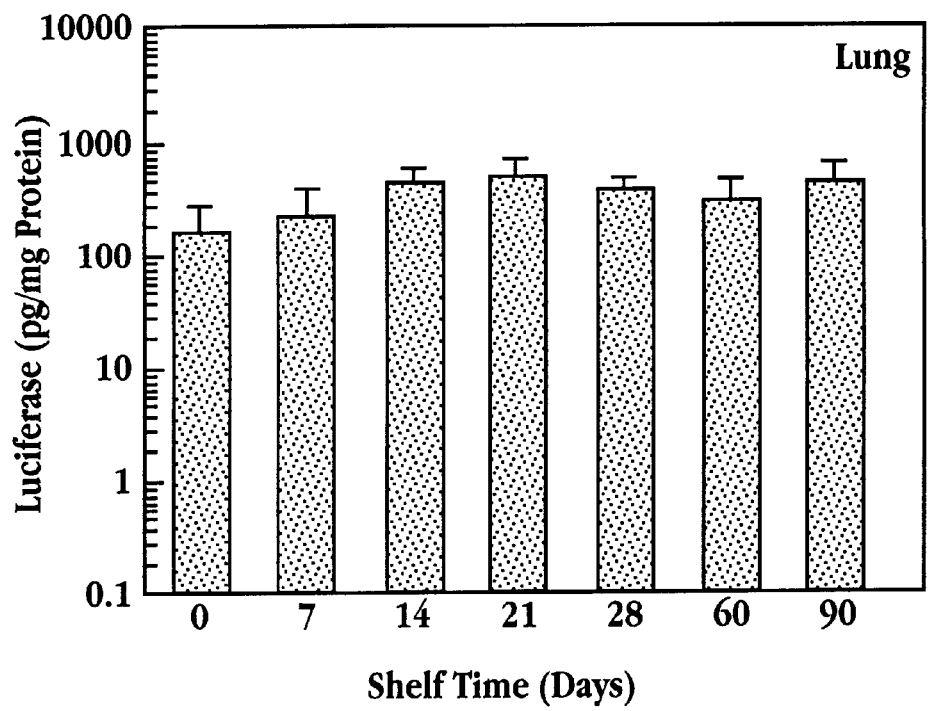
FIGS. 11A–11B show luciferase expression in the lung (FIG. 11A) and the liver (FIG. 11B) as a function of time in days for plasmid-liposome complexes stored alt 4° C.
Figure 11B:
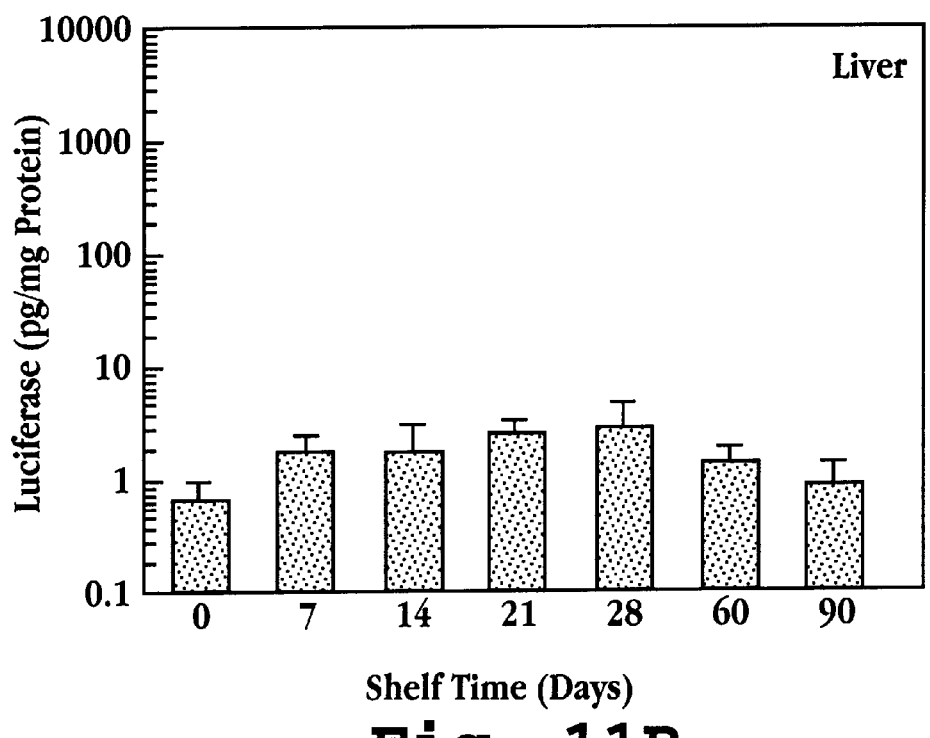

As seen in FIGS. 11A–11B, luciferase expression in the lung (FIG. 11A) and the liver FIG. 11B) remain constant as a function of storage time of the complexes. It is clear that he complex retained the ability to express the encoded gene for the 90 day test period. Accordingly, in one embodiment of the invention that the complex is characterized by the ability to retain more than 50% of the expression activity measured at day 0 for at least 30 days, more preferably for 90 days.

Figure 12:
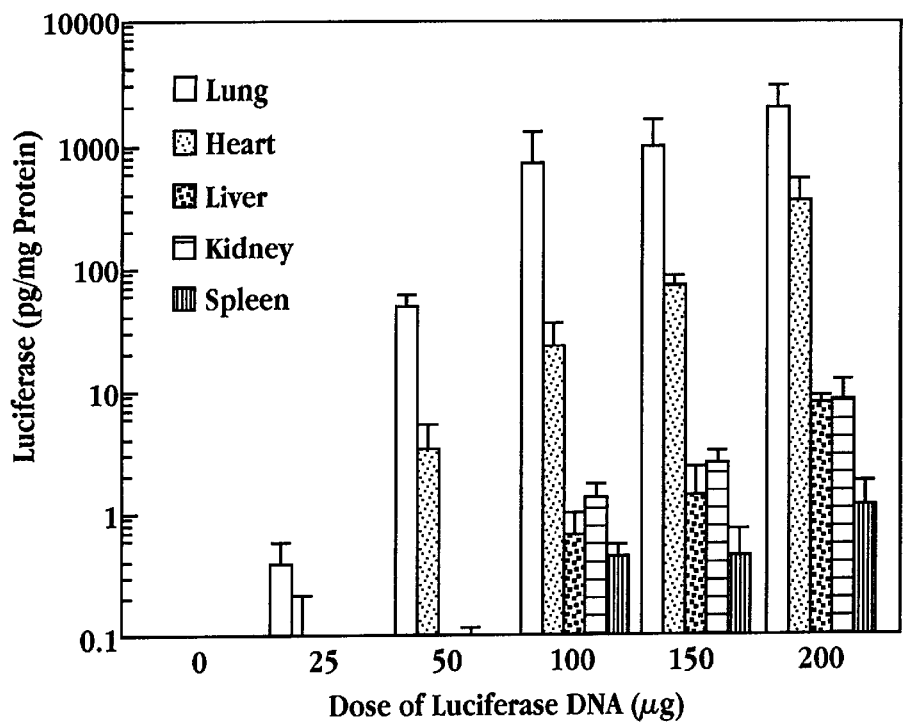
FIG. 12 shows luciferase in various tissues, in pg/mg protein, at 24 hours after intravenous administration in mice of plasmid-liposome complexes, as a function of micrograms of luciferase-carrying plasmid.

A dose-response study was performed using plasmid-liposome complexes prepared as described in Example 1. The plasmid-liposome complex was administered intravenously in mice at five dosage levels of plasmid: 25, 50, 200 250 and 200 µg. Twenty-four hours after administration, luciferase expression in the lung, heart, liver, kidney and spleen was measured, and the results are shown in FIG. 12. The luciferase expression measured was proportional to the dose administered, with the highest expression in the lung.

The systemic luciferase expression 24 hours following administration of the plasmid-liposome complex in mice is

TABLE 4

| | Condensing Agent[1] | | | | | | | | |
|---|---|---|---|---|---|---|---|---|---|
| condensing agent | poly-1-glutamine | | | melittin | | | polymyxin B | | |
| Formulation No. | 21 | 22 | 23 | 24 | 25 | 26 | 27 | 28 | 29 |
| pNSL plasmid, µg | 100 | 100 | 100 | 100 | 100 | 100 | 100 | 100 | 100 |
| µg condensing agent | 50 | 100 | 200 | 50 | 100 | 200 | 50 | 100 | 200 |
| µmoles liposome lipids[2] | 1.4 | 1.4 | 1.4 | 1.4 | 1.4 | 1.4 | 1.4 | 1.4 | 1.4 |
| µg plasmid/µg condensing agent | 2 | 1 | 0.5 | 2 | 1 | 0.5 | 2 | 1 | 0.5 |
| nmoles lipids/µg plasmid | 14 | 14 | 14 | 14 | 14 | 14 | 14 | 14 | 14 |

Figure 13:
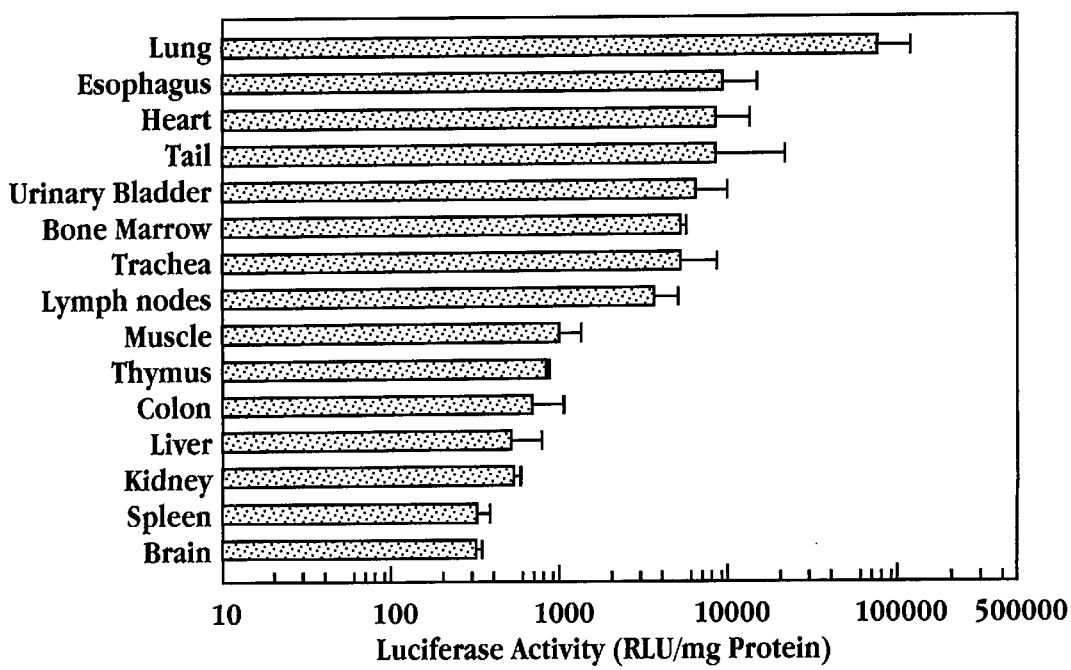
FIG. 13 shows luciferase activity, in RLU/mg protein, in various tissues 24 hours after intravenous administration of plasmid-liposome complexes.

[1]In vivo results for each formulation number shown in FIGS. 10A–10E.
[2]Liposomes prepared from 1:1 mole ratio of DDAB:cholesterol.

shown in FIG. 13. The plasmid-liposome complex distributes widely, as evidenced by luciferase expression in the bone marrow, lymph nodes and brain.

In another study performed in support of the invention, detailed in Example 3, mice bearing metastatic Lewis lung tumors were treated with plasmid-liposome complexes. After tumor inoculation, the mice were treated with one of eight treatment regimens set forth in Table 5 in Example 3. The treatments included administration of plasmid-liposomes complexes prepared using plasmids carrying genes encoding for p53 (pCMVp53) and interleukin 2 (pCMVIL2) and a combination treatment of ganciclovir and plasmid-liposome complexes prepared with a pHSVtk (herpes Simplex Virus thymidine kinase) plasmid. A control group of animals received saline, and comparative groups of animals received complexes prepared with the pNSL plasmid encoding for lucifrease (Example 1) or ganciclovir alone.

Figure 14A:
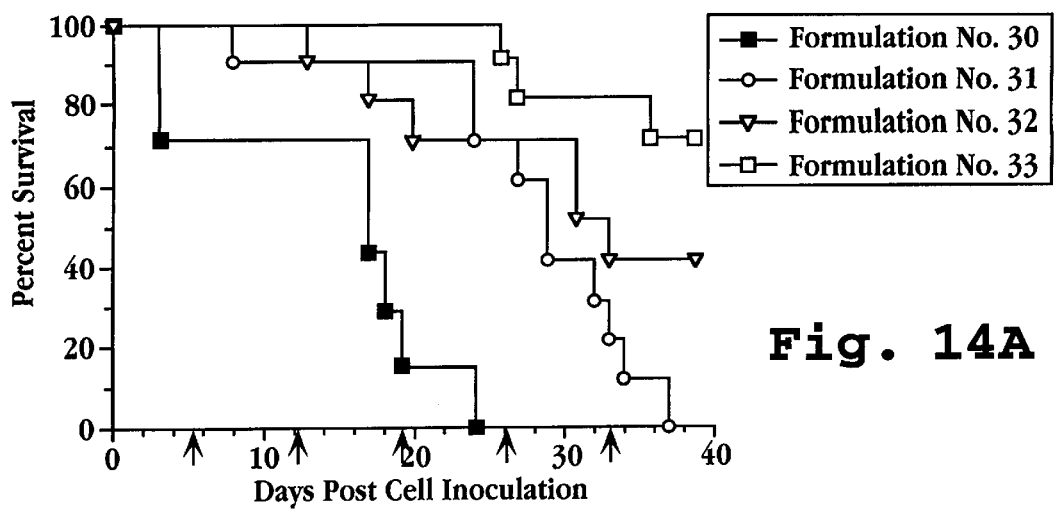
FIGS. 14A–14B show percent of surviving animals as a function of days post inoculation with Lewis lung metastasis, for animals treated with plasmid-liposome complexes including the plasmids pHSVtk (FIG. 14A), pCMVp53 (FIG. 14B) and pCMVIL2 (FIG. 14C)
Figure 14B:
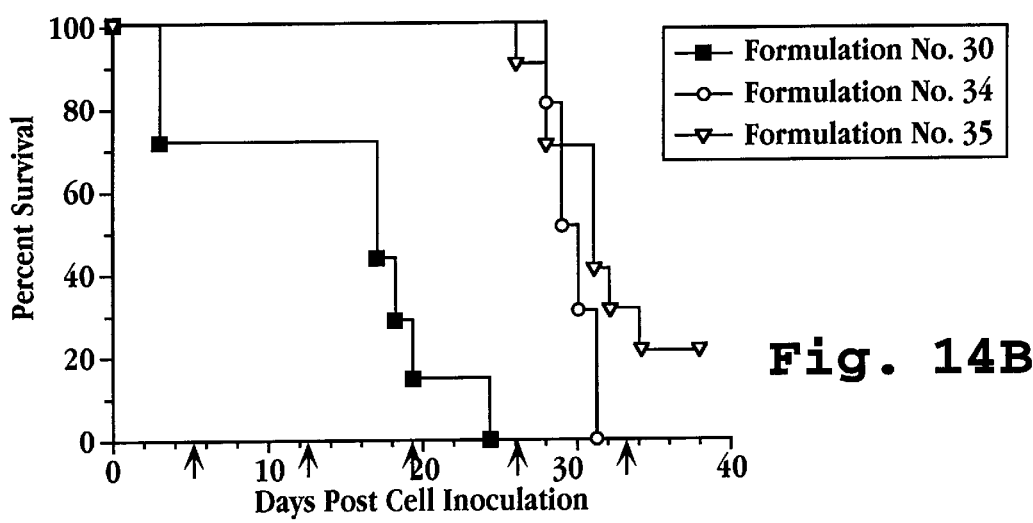
Figure 14C:
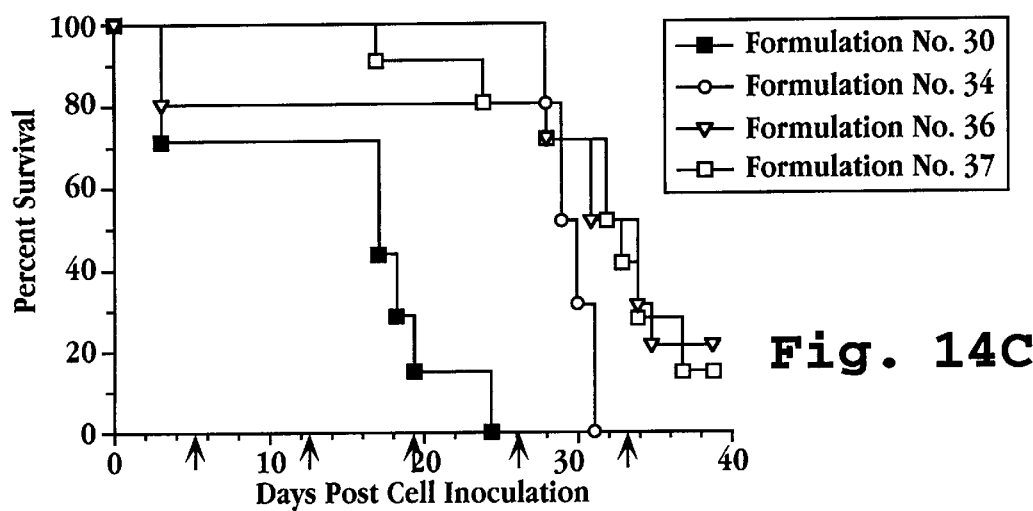

FIGS. 14A–14C show the percent of surviving animals as a function of days post tumor-cell inoculation. In all of FIGS. 14A–14C, the animals treated with saline are represented with the closed squares. As seen, all of the saline-treated animals died by 24 days after tumor inoculation. In FIG. 14A, the animals treated with complexes including the 50 μg (solid inverted triangles) and 75 μg (open squares) pHSVtk plasmid and with ganciclovir are shown. All of the animals treated with ganciclovir alone (open circles) died by day 37. In contrast, the animals treated with the combination therapy of liposome-plasmid complexes and ganciclovir fared better, with 70% of those treated with the higher plasmid dose surviving the study.

FIG. 14B shows the percent survival of animals treated with plasmid-liposome complexes including pCMVp53 (solid inverted triangles) and pNSL (encoding for luciferase) (open circles). As seen, 20% of the animals treated with complexes including the plasmid encoding for the p53 gene survived the duration of the study, whereas the saline-treated animals (closed squares) and the animals treated with the pNSL, plasmid encoding for luciferase-reporter gene died.

FIG. 14C shows the results for animals treated with complexes including the pCMVIL2 plasmid, administered at 50 μg plasmid DNA (inverted solid triangles) and 75 μg plasmid DNA (open squares). As seen, between about 15–20% of the animals survived at the end of the treatment period, whereas left untreated (saline control, solid squares) all of the animals died by day 24. Similarly, animals treated with complexes including the luciferase-encoding pNSL plasmid (open circles) died by day 31.

Figure 15:
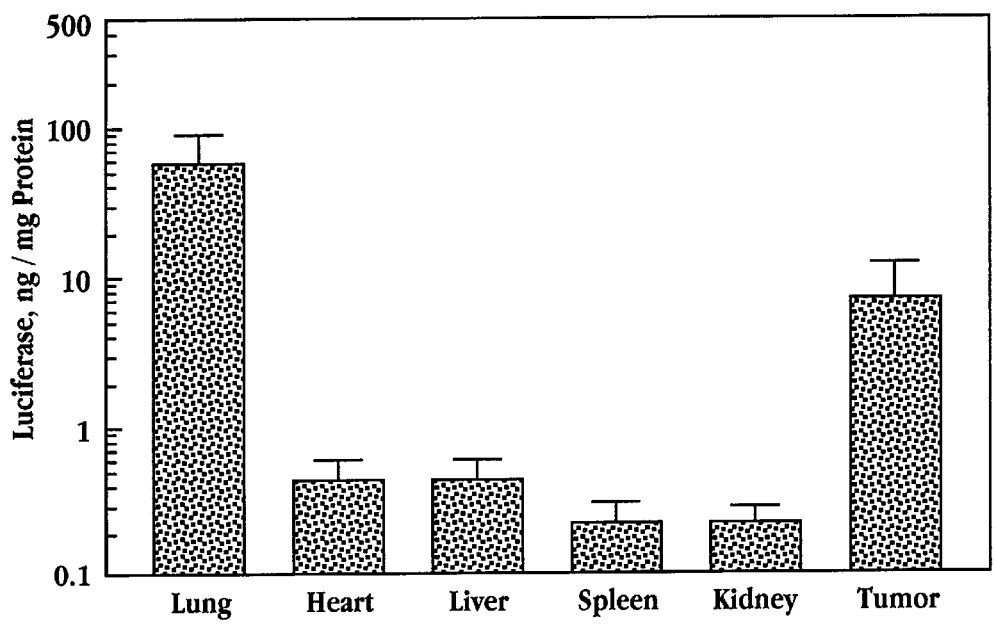
FIG. 15 is a plot showing the body weight, in grams, of mice following administration of plasmid-liposome complexes prepared with a pNSL plasmid encoding for luciferase as a function of time in days. The mice were treated on days 1, 8, 15, 22 and 28, as indicated by the arrows in the plot, with saline (plus symbols), and plasmid-liposome complexes at dosages of 50 μg plasmid (open circles), 75 μg plasmid (closed triangles) and 100 μg plasmid (open, inverted triangles)

Formulation number 34 from Table 5 in Example 3, namely the plasmid-liposome complex with the pNSL luciferase-encoding gene, was administered to mice at dosages of 50 μg plasmid/0.7 μmol lipid, 75 μg plasmid/1.05 μmol lipid and 100 μg plasmid/1.4 μmol lipid and the body weight of the mice was monitored as an indication of toxicity of the formulation. As seen in FIG. 15, mice treated on days 1, 8, 15, 22 and 28, as indicated by the arrows in the plot, with the complexes had a small loss of weight after the first dose, but recovered any weight loss within a few days. The symbols in the figure are as follows: mice treated with saline (plus symbols) and mice treated with plasmid-liposome complexes at dosages of 50 μg plasmid (open circles), 75 μg plasmid (closed triangles) and 100 μg plasmid (open, inverted triangles).

Figure 16:
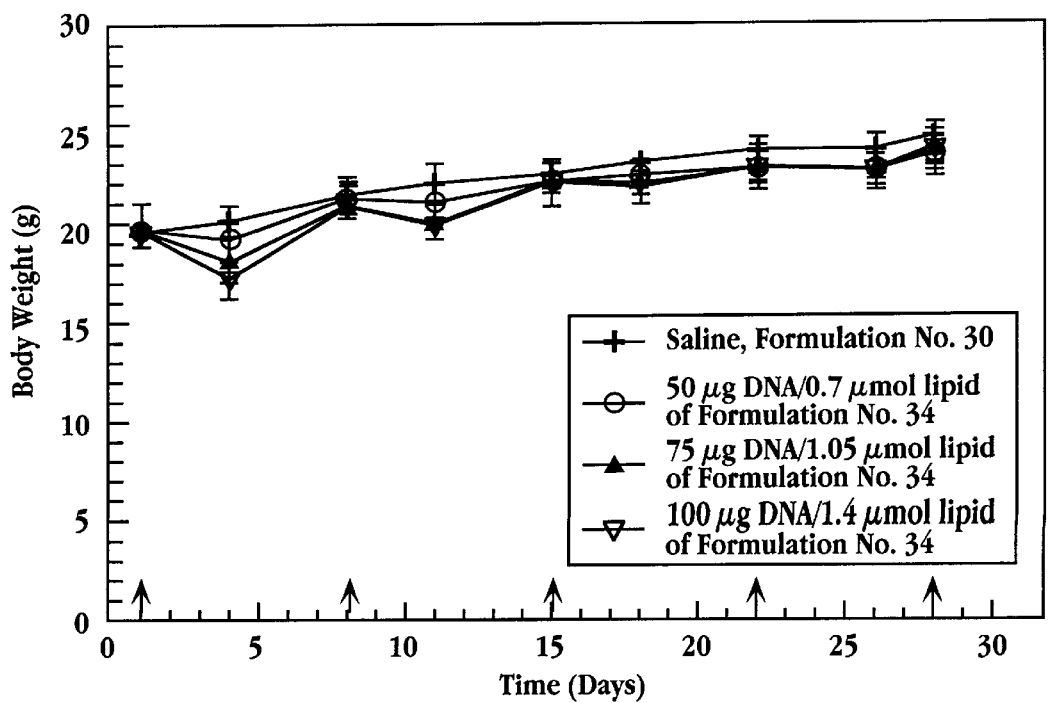
FIG. 16 is a plot showing luciferase expression, in ng/mg protein, in various mice tissues 24 hours after administration of plasmid-liposome complexes prepared with pNSL plasmid encoding for luciferase to tumor-bearing mice (metastasis model of Lewis Lung Tumor).

In another study using the Lewis lung tumor model, the pNSL-luciferase-plasmid-liposome complex was administered to mice and luciferase expression in various tissues was examined 24 hours after administration of plasmid-liposome complexes. As seen in FIG. 16, the highest luciferase expression was observed in the lung and in the tumors.

From the foregoing, it can be appreciated how various features and objects of the invention are met. Plasmid-liposome complexes prepared in accordance with the method of the invention form a substantially homogeneous population having sizes, of less than about 200 nm, as evidenced by dynamic light scattering. The complexes are stable for 90 days, with no aggregation of complexes, as evidenced by dynamic light scattering. Importantly, the transfection activity of the complexes is also stable, where the complexes retain more than 50% of transfection efficiency after storage for at least 30 days at 4° C.

IV. EXAMPLES

The following examples illustrate methods of preparing, characterizing, and using the plasmid-liposome complexes of the present invention. The examples are in no way intended to limit the scope of the invention.

Materials and Methods

A. Lipids

Dimethyldioctadecylammonium (DDAB) was purchased from Avanti Polar Lipids, Inc. (Birmingham, Ala.). Cholesterol, greater than 99% pure, was obtained from Nu-Chek (Elysian, Minn.).

B. Polycationic Condensing Agents

Total histone, consisting of a mixture of histones, including H1, H2, H3 and H4, histone H1 and histone H4 were obtained from Boehringer Mannheim (Indianapolis, Ind.).

Poly-l-glutamine, melittin and polymyxin B sulfate were obtained from Sigma Chemical Co. (St. Louis, Mo.).

C. Methods: Dynamic Light Scattering

Size distribution measurements were obtained by dynamic light scattering (DLS) using a Coulter N4MD instrument, operated according to the manufacturer's, instructions. The results were expressed as the mean diameter in nm and standard deviation of a Gaussian distribution of particles by relative volume.

EXAMPLE 1

Preparation of Plasmid-Liposome Complex

A. Preparation of pNSL Plasmid

A pNSL plasmid encoding for luciferase was constructed from two commercially available plasmids, pGFP-N1 plasmid (Clontech, Palo Alto, Calif.) and pGL3-C (Promega Corporation, Madison, Wis.).

The pGL3-C was cut with XbaI and blunt-end ligated using the Klenow fragment of $E.\ coli$ DNA polymerase. It was then cut with HindIII and the 1689-bp fragment, carrying the luciferase gene, was gel-purified. The pGFP-N1 plasmid was cut with SmaI and HindIII and the 4.7 kb fragment, isolated from an agarose gel, was ligated with the luciferase fragment. JM109 $E.\ Coli$ cells were transformed and 20 colonies were selected; about half of then showed the presence of inserts; 8 clones with inserts were cut with NamHI and XhoI to further confirm the presence of the luciferase gene; 7 of them were positive.

B. Preparation of Cationic Liposomes

Cationic liposomes were prepared according to standard procedures by dissolving 10 μmol DDAB and 10 μmol cholesterol in an organic solvent containing primarily CHCl$_3$. The lipids were dried to a thin film by rotation under reduced pressure. The lipid film was hydrated by addition of distilled water to form a suspension of liposomes at a concentration of 20 μmole/ml. The liposomes were sized by sonication or by sequential extrusion through Nucleopore polycarbonate membranes with pore sizes of 0.4 μm, 0.2 μm, 0.1 μm and 0.05 μm to obtain liposomes of less than about 200 nm in size (Nucleopore, Pleasanton, Calif.).

C. Preparation of Condensed Plasmid

The DNA plasmid pNSL encoding for luciferase, prepared as described above, was condensed according to the following procedure. 400 µl of the plasmid (1 mg/ml in distilled water) was diluted with 310 µl distilled water and then mixed with 90 µl of 50% glucose. 100 µl of a polycationic condensing agent (total histone, histone H1, histone H4, poly-l-glutamine, melittin or polymyxin B) from a stock solution of 1 mg/ml in distilled water was added to the plasmid solution slowly with stirring. The mixture was stirred for 10 minutes.

D. Preparation of Complex

Plasmid-liposome complexes having a liposome lipid/plasmid ratio of 14 nmole lipid/µg plasmid was prepared by diluting 280 µl of the liposome suspending with 350 µl of distilled water and then adding 70 µl of 50% glucose. The suspension of condensed plasmids was slowly added to the diluted cationic liposome suspension with continuous stirring for 10 minutes.

EXAMPLE 2

In vivo Transfection Procedure

In vivo transfection with the plasmid-liposome complexes was conducted with BALB/c mice obtained from Simonsen (Gilroy, Calif.). Each plasmid-liposome complex formulation was injected via tail vein into 3 mice. The mice were sacrificed 24 hours after injection and tissues (lung, liver, spleen, kidney, heart) were collected following perfusion with heparinized PBS (4 C) under anesthesia.

At a temperature of between 0–4° C., 0.75 µl cell lysis reagent (Promega, Madison, Wis.) was added to each tissue, and the tissue was homogenized for 1 minute at 20,000 rpm. The supernatant was removed to a microcentrifuge tube and spun at 10,000 g for 5 minutes. The supernatant was collected for luciferase and protein assays. 20 µl of each sample was measured immediately by a luminometer (100 µl of luciferin and ATP containing assay buffer, 10 second measurement). The relative light unit was normalized by the amount of protein in the extracts.

EXAMPLE 3

In vivo Transfection Tumor-Bearing Mice

A. Preparation of Plasmid-Liposome Complexes

Plasmid-liposome complexes were prepared according to the procedure of Example 1 using the following plasmids: pNSL encoding for luciferase, prepared as described in Example 1, and pCMVp53, pCMVIL2 and pHSVtk (all commercially available).

B. Tumor Inoculation

Eighty B6C3-F1 male mice were obtained from Taconic Farms (German Town, N.Y.) and allowed to acclimate for 3 days prior to initiation of the experiment. Animals were housed in appropriate isolated caging with ad lib sterile rodent food and acidified water and a 12:12 light:dark cycle. Animals were randomized into treatment groups prior to inoculation of tumors based on body weight. Animals were randomized into treatment groups prior to inoculation of tumors.

All the animals were observed daily for general well-being. The animals were weighed prior to inoculation of tumor cells and twice weekly thereafter. Animals observed to have a 15% or greater weight loss from their starting weight, or any animal in distress, was euthanized and examined for the presence and size of metastatic foci in the lung, liver and spleen.

Tumors were inoculated by taking growing Lewis lung tumors from other B6C3-F1 mice by sterile surgical harvest after euthanasia. The tumors were mechanically minced as finely as possible and briefly digested in an enzyme mix of collagenase, protease and DNAse at 37° C. After digestion and washing in media (RPMI+15% FCS) cells were counted with a hemocytometer. Cells were spun down and resuspended in media at $10^6$ cells per ml ($10^5$ cells per 0.1 ml injection). The resuspended cells were drawn into individual syringes (0.1 ml, with continuous mixing) for intravenous injection into the tail vein of each animal.

C. Treatment

Animals were treated, beginning 3 days after inoculation with tumor cells, with one of the eight regimens set forth in Table 5. The 10 animals in each group were treated 5 times at one-week intervals, except as indicated for the ganciclovir treatment group no. 30 and for the animals receiving ganciclovir as part of a combination therapy (group nos. 32, 33).

TABLE 5

| Formulation No. | Composition |
| --- | --- |
| 30[1,2,3,4] | saline, 0.1 ml IV |
| 31[1] | ganciclovir, 100 µg/kg IP twice daily for 6 days for 5 weeks |
| 32[1] | liposome/pHSVtk complex, 50 µg DNA/mouse + ganciclovir 100 µg/kg twice daily for 6 days after each administration of the plasmid/liposome complex |
| 33[1] | liposome/pHSVtk complex, 75 µg DNA/mouse + ganciclovir 100 µg/kg twice daily for 6 days after each administration of the plasmid/liposome complex. |
| 34[2,3,4,5] | liposome/pNSL (luciferase encoding) complex; varying doses of 50, 75, 100 µg plasmid |
| 35[2] | liposome/pCMVp53 complex, 75 µg DNA/mouse |
| 36[3] | liposome/pCMVIL2 complex, 50 µg DNA/mouse |
| 37[3] | liposome/pCMVIL2 complex, 75 µg DNA/mouse |

[1]data presented in FIG. 14Adata presented in FIG. 14Bdata presented in FIG. 14Cdata presented in FIG. 15data presented in FIG. 16

Twenty-four hours after the last treatment, surviving animals were euthanized for tissue and tumor harvest and examination. The percent of surviving animals for each treatment group are shown in FIGS. 14A–14C. Toxicity of formulation no. 34 is shown in FIG. 15 and luciferase expression of formulation no. 34 is shown in FIG. 16.

Although the invention has been described with respect to particular embodiments, it will be apparent to those skilled in the art that various changes and modifications can be made without departing from the invention.

It is claimed:

1. A composition of plasmid-liposome complexes for use in transfecting a host cell with a gene contained in a plasmid, comprising condensed plasmid molecules, said molecules condensed with a polycationic condensing agent and suspended in a low-ionic strength aqueous medium, and cationic liposomes comprising a cationic vesicle-forming lipid, wherein said complexes have a ratio of liposome lipid to plasmid of greater than 5 nmole liposome lipid/µg plasmid and less than 25 nmole liposome lipid/µg plasmid and have a substantially homogeneous size of less than about 200 nm.

2. The composition of claim 1, wherein the condensed plasmid molecules are DNA plasmid molecules containing a gene selected from the group consisting of genes encoding for cystic fibrosis transmembrane conductance regulator, Factor VIII, interleukin-2 and p53.

3. The composition of claim 1, wherein the condensing agent is a polycation selected from the group consisting of histones, poly-l-glutamine, protamine, melittin and polymyxin B.

4. The composition of claim 3, wherein the condensing agent is a histone selected from total histone, histone 1 and histone 4.

5. The composition of claim 1, wherein the ratio of liposome lipid to plasmid is between 8–18 nmole liposome lipid/µg plasmid.

6. The composition of claim 1, wherein the low-ionic strength aqueous medium is prepared from a non-ionic osmotic solute.

7. The composition of claim 6, wherein said solute is selected from the group consisting of glucose, sucrose and dextran.

8. The composition of claim 1, wherein the cationic liposomes are composed of a cationic vesicle-forming lipid selected from the group consisting of dimethyldioctadecylammonium (DDAB), 1,2-diolelyloxy-3-(trimethylamino) propane (DOTAP), N-[1-(2,3 , -ditetradecyloxy)propyl]-N, N-dimethyl-N-hydroxyethylammonium bromide (DMRIE), N-[1-(2,3,-dioleyloxy)propyl]-N,N-dimethyl-N-hydroxy ethylammonium bromide (DORIE), N-[1-(2,3-dioleyloxy) propyl]-N,N,N-trimethylammonium chloride (DOTMA), and 3β[N-(N',N'-dimethylaminoethane) carbamoly] cholesterol (DC-Chol).

9. The composition of claim 1, wherein the cationic liposomes further include a neutral vesicle forming lipid.

10. The composition of claim 1, wherein the cationic liposomes further include cholesterol.

11. The composition of claim 1, wherein the cationic liposomes have a surface coating of hydrophilic polymer chains formed by derivatizing a vesicle-forming lipid, a hydrophilic polymer.

12. The composition of claim 11, wherein at least a portion of the hydrophilic polymer is joined to the vesicle-forming lipid by a bond effective to release the hydrophilic polymer chains in response to an existing or an induced physiologic condition.

13. The composition of claim 11, wherein the plasmid-liposome complexes further include a ligand attached to distal ends of the hydrophilic polymer chains for ligand-specific binding to a receptor molecule on a target cell surface.

14. The composition of claim 11, wherein the hydrophilic polymer is polyethyleneglycol.

* * * * *